United States Patent [19]

Werner et al.

[11] 4,280,049
[45] Jul. 21, 1981

[54] X-RAY SPECTROMETER

[75] Inventors: Helmut W. W. Werner; Antonius W. Witmer; Wilhelmus F. Knippenberg, all of Eindhoven, Netherlands

[73] Assignee: U.S. Philips Corporation, New York, N.Y.

[21] Appl. No.: 42,269

[22] Filed: May 24, 1979

[30] Foreign Application Priority Data

Jun. 12, 1978 [NL] Netherlands ............... 7806330

[51] Int. Cl.³ .................................. G01M 23/00
[52] U.S. Cl. ........................ 250/310; 250/272; 250/399
[58] Field of Search .................. 250/399, 310, 272

[56] References Cited

FOREIGN PATENT DOCUMENTS 1558130 3/1968 France ........................ 250/272

Primary Examiner—Harold A. Dixon
Attorney, Agent, or Firm—Thomas A. Briody; Robert T. Mayer; Paul R. Miller

[57] ABSTRACT

An X-ray spectrometer which is arranged inside an evacuatable housing and which comprises a wavelength dependent X-ray detection system and, for irradiating the specimen to be examined, an electron source with an electron deflection system for generating an electron beam and an X-ray source for generating an X-ray beam. The X-ray source consists of an anticathode on which the electron beam can be directed by the electron deflection system in order to generate the X-ray beam.

7 Claims, 1 Drawing Figure

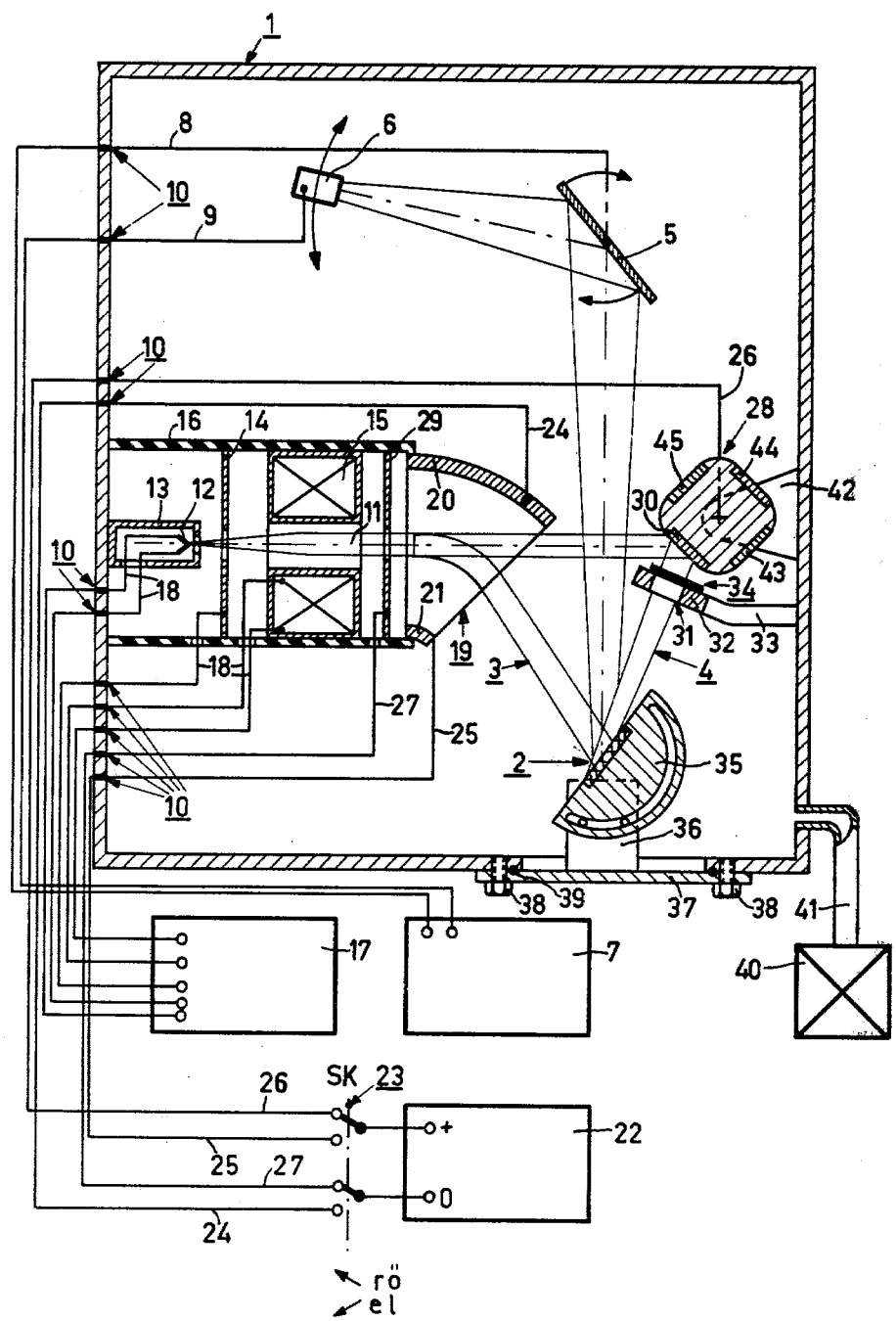

X-RAY SPECTROMETER

BACKGROUND OF INVENTION

The invention relates to an X-ray spectrometer which is arranged in an evacuatable housing and which comprises a wavelength-dependent X-ray detection system and—for irradiating a specimen to be examined—an electron source for generating an electron beam and an X-ray source with an anticathode on which the electron beam can be directed by means of an electrostatic deflection system in order to generate an X-ray beam.

An X-ray spectrometer of this kind is particularly suitable for chemical analysis because the X-radiation generated in the specimen being examined contains characteristic X-radiation which originates from the chemical elements present in the specimen. By wavelength-dependent measurement and analysis of the X-radiation generated, elements emitting characteristic X-radiation can be indentified and quantized by measurement of the intensity of the relevant radiation. For the examination of a specimen containing light elements, such as B, C, Na, Al or Mg, an electron beam is preferably used for irradiation; and for the examination of a specimen containing heavier elements, an X-ray beam is preferably used for irradiation.

French Patent Specification No. 1,558,130 discloses an X-ray spectrometer of the described kind in which the electrostatic deflection device can be used to direct the electron beam onto either the specimen to be examined or onto the anticathode which is in this case situated opposite the specimen.

It is a drawback of the described known X-ray spectrometer that, in order to irradiate the specimen by means of X-rays, electrons supplied by the electron source must first be accelerated, after which the accelerated electrons are deflected onto the anticathode. One of the two voltage sources required for this purpose is used for the deflection of accelerated electrons, which requires comparatively large electric fields and hence comparatively high electric voltages.

SUMMARY OF INVENTION

The present invention has for its object to eliminate these drawbacks. To this end, an X-ray spectrometer in accordance with the invention is characterized in that the electrostatic deflection system is arranged so that, when the deflection system is switched off, the electron beam can reach the anticathode in an unobstructed manner, while the electron beam can be incident on the specimen when the deflection system is switched on. Because the electrostatic deflection system is switched off during the irradiation of the specimen by means of an X-ray beam, only one power supply source is required which is used for deflecting the electron beam to the specimen during electron irradiation, and which is used to accelerate the electron beam towards the anticathode during irradiation by means of an X-ray beam.

BRIEF DESCRIPTION OF DRAWING

The invention will be described in detail hereinafter, by way of example, with reference to the accompanying drawing which diagrammatically shows a preferred embodiment of the X-ray spectrometer in accordance with the invention.

DETAILED SPECIFICATION

In the X-ray spectrometer, arranged in an evacuatable housing 1, a specimen 2 to be examined is irradiated (in a manner yet to be described) by an electron beam 3 or an X-ray beam 4. In the specimen 2, X-radiation is generated which at least partly consists of characteristic X-radiation originating from chemical elements present in the specimen 2. For the identification of these elements, the X-radiation generated is measured in a wavelength-dependent manner by means of a known X-ray detection system comprising an analysis crystal 5 and an X-ray detector 6 which are arranged inside the X-ray spectrometer (as diagrammatically shown) to be rotatable with respect to each other as well as with respect to the specimen 2. The relative position of the parts which are rotatable with respect to each other is measured (in a known manner which will not be elaborated herein) and the relevant measuring data are applied for processing, together with measuring data originating from the detector 6, to an analysis apparatus 7 by means of a cable 8, 9, respectively, which is passed through a wall of the housing 1 by vacuumtight passages 10.

An electron beam 11 required for irradiation is generated in known manner by means of a filament 12 which is arranged inside a Wehnelt electrode 13 and a first anode 14 and an electromagnetic lens 15 which are connected to a cylinder 16 of an insulating material. For power supply, these components are connected to a power supply device 17 by means of cables 18 which are passed through a wall of the housing 1 by vacuumtight passages 10. The electron beam 11 is directed onto the specimen 2 by means of an electron deflection unit 19 which comprises cylindrical, conductive plates 20 and 21 which are connected to a high-voltage power supply unit 22 by means of a switch 23 and cables 24 and 25 which are passed through the wall of the housing 1 by vacuumtight passages 10. When the switch 23 is switched over, the high-voltage power supply unit 22 is connected to an anticathode 30 which is mounted on a support 28 and also to a second anode 29, by means of cables 26 and 27, respectively, which are passed through a wall of the housing 1 by vacuumtight passages 10. Thus, the electron beam 11 is not influenced by the deflection system 19 but is accelerated by the high voltage between the second anode 29 and the anticathode 30. In the anticathode 30 X-radiation is generated, the part thereof which is enclosed by the beam 4 being used for irradiating the specimen 2.

The beam 4 is stopped by an aperture 31 in a collimator 32 which is connected to a wall of the housing 1 by means of a bracket 33. On the aperture 31 there is provided a removable electron filter 34 of, for example, 100 $\mu$m Al, in order to prevent electrons of the beam 11 which are reflected by the anticathode 30 from being incident on the specimen 2. The spectrum of reflected electrons generally exhibits a large energy spread. Inaccuracies in the analysis of the X-radiation generated in the specimen which are caused by this energy spread in the case of simultaneous irradiation by reflected electrons and X-radiation are thus avoided.

The specimen 2 is arranged on a specimen holder 35 which is adjustably arranged on a base 36 which is connected to a lid 37 which is removably connected, by means of bolts 38, to a wall of the housing 1. An O-ring 39 provides vacuumtight sealing. The specimen holder 35 is rotatable about an axis perpendicular to the plane of the drawing, so that different values can be imparted to the angle between the specimen surface and the incident radiation (the angle of incidence). If the angle of incidence is small, only a surface layer of small "depth" is examined due to the comparatively small penetration depth of X-radiation and electron radiation. A "depth" analysis is obtained by performing analysis at different angles of incidence. When the lid 37 is fitted prior to the start of an examination, the housing 1 of the spectrometer is evacuated by means of a pump 40 which is connected to the housing 1 by means of a pumping duct 41. The evacuation is influenced to only a comparatively small extent by the degassing of the components arranged inside the housing 1, because the X-ray source required for irradiation consists only of the support 28 with the anticathode 30, so that it is conparatively small.

The support 28 is rotatedly arranged inside the housing 1 by means of a frame 42 which is connected to a wall of the housing 1. In order to exchange the X-ray source during examination, because a new or other anticathode is required, without interruption of the analysis, it is merely necessary to rotate the support 28 which in this case comprises four anticathodes 30, 43, 44 and 45. Another anticathode is desirable, for example, if it appears during an analysis that the specimen 2 to be examined contains an element which is also contained in the anticathode, so that it causes characteristic X-radiation of the element in the beam 4. The anticathode may also be (not shown) a rotary anticathode having a circumference which is provided with a path of a material also used for the manufacture of one of the anticathodes 30, 43, 44 or 45. When such a form of anticathode is used, the X-ray source may be loaded to a comparatively high degree.

What is claimed is:

1. An X-ray spectrometer comprising an evacuated housing, a wavelength dependent X-ray detection system, electron means for generating an electron beam to irradiate a specimen to be examined, deflection means for directing said electron beam, an X-ray source having an anticathode on which said electron beam may be directed by said deflection means to generate an X-ray beam for irradiating said specimen, wherein said electron beam is directed to said anticathode when said deflection means is switched off, and wherein said electron beam is directly incident on said specimen when said deflection means is switched on, and means arranged between said anticathode and said specimen in the incident X-ray beam path for filtering reflected electrons from said anticathode and passing only said X-rays to said specimen.

2. An X-ray spectrometer according to claim 1, wherein said anticathode is arranged in the direct electron beam path, and the specimen is arranged in the deflected electron beam path.

3. An X-ray spectrometer according to claim 1, wherein support means are provided for mounting at least one anticathode.

4. An X-ray spectrometer according to claim 3, wherein said support means rotatably mount a plurality of anticathodes which can be individually located for generating said X-ray beam.

5. An X-ray spectrometer according to claim 4, wherein means for rotating said specimen is provided.

6. An X-ray spectrometer according to claim 1, wherein said deflection means are electrostatic.

7. An X-ray spectrometer according to claim 1, wherein means for rotating said specimen is provided.

* * * * *